United States Patent
Krimsky

(10) Patent No.: US 11,006,852 B2
(45) Date of Patent: May 18, 2021

(54) SYSTEMS, METHODS, AND COMPUTER-READABLE MEDIA OF ESTIMATING THORACIC CAVITY MOVEMENT DURING RESPIRATION

(71) Applicant: Covidien LP, Mansfield, MA (US)

(72) Inventor: William S. Krimsky, Forest Hill, MD (US)

(73) Assignee: COVIDIEN LP, Mansfield, ME (US)

( * ) Notice: Subject to any disclaimer, the term of this patent is extended or adjusted under 35 U.S.C. 154(b) by 347 days.

(21) Appl. No.: 16/214,267

(22) Filed: Dec. 10, 2018

(65) Prior Publication Data

US 2019/0175057 A1 Jun. 13, 2019

Related U.S. Application Data

(60) Provisional application No. 62/597,200, filed on Dec. 11, 2017.

(51) Int. Cl.
*A61B 5/05* (2021.01)
*A61B 5/06* (2006.01)
(Continued)

(52) U.S. Cl.
CPC .............. *A61B 5/062* (2013.01); *A61B 5/066* (2013.01); *A61B 5/1135* (2013.01); *A61B 5/742* (2013.01);
(Continued)

(58) Field of Classification Search
CPC combination set(s) only.
See application file for complete search history.

(56) References Cited

U.S. PATENT DOCUMENTS

| 5,081,993 A | 1/1992 | Kitney et al. |
| 5,557,711 A | 9/1996 | Malzbender |

(Continued)

FOREIGN PATENT DOCUMENTS

| EP | 1504713 A1 | 2/2005 |
| EP | 1717758 A2 | 11/2006 |

(Continued)

OTHER PUBLICATIONS

Kiraly A P et al: "Three-dimensional human airway segmentation methods for clinical virtual bronchoscopy", Academic Radiology, Reston, VA, US, vol. 9, No. 10, pp. 1153-1168, Sep. 1, 2002.

(Continued)

*Primary Examiner* — Joel F Brutus

(57) ABSTRACT

A system for visualizing movement of structures within a patient's chest is described herein. The system includes an electromagnetic tracking system, a computing device and a display. The computing device includes a processor configured generate a 3D model of an interior of the patient, obtain positions of EM sensors for the 3D model, determine positions of the EM sensors at intervals during the respiratory cycle, determine positions of the EM sensors at maximum tidal volume and minimum tidal volume, determine differences between the positions of the EM sensors at maximum tidal volume and for the 3D model, generate a 3D model at maximum tidal volume based on the differences between the positions of the EM sensors at maximum tidal volume and for the 3D model, and store in memory the 3D model at maximum tidal volume.

20 Claims, 7 Drawing Sheets

(51) Int. Cl.
*A61B 5/00* (2006.01)
*G06T 17/00* (2006.01)
*A61B 5/113* (2006.01)
*A61B 1/267* (2006.01)

(52) U.S. Cl.
CPC ............ *G06T 17/00* (2013.01); *A61B 1/2676* (2013.01); *G06T 2210/41* (2013.01)

(56) References Cited

U.S. PATENT DOCUMENTS

| | | | |
|---|---|---|---|
| 5,898,793 | A | 4/1999 | Karron et al. |
| 6,016,439 | A | 1/2000 | Acker |
| 6,315,724 | B1 | 11/2001 | Berman et al. |
| 6,556,696 | B1 | 4/2003 | Summers et al. |
| 7,202,463 | B1 | 4/2007 | Cox |
| 7,233,820 | B2 | 6/2007 | Gilboa |
| 7,420,555 | B1 | 9/2008 | Lee |
| 7,480,398 | B2 | 1/2009 | Kleen et al. |
| 7,830,378 | B2 | 11/2010 | Inoue et al. |
| 7,901,348 | B2 | 3/2011 | Soper et al. |
| 8,116,847 | B2 | 2/2012 | Gattani et al. |
| 8,165,367 | B2 | 4/2012 | Inoue et al. |
| 8,463,006 | B2 | 6/2013 | Prokoski |
| 8,493,323 | B2 | 7/2013 | Griffin |
| 8,696,685 | B2 | 4/2014 | Gilboa |
| 9,254,112 | B2 | 2/2016 | Tryggestad et al. |
| 2001/0031920 | A1 | 10/2001 | Kaufman et al. |
| 2002/0049375 | A1 | 4/2002 | Strommer et al. |
| 2002/0137014 | A1 | 9/2002 | Anderson et al. |
| 2005/0107679 | A1 | 5/2005 | Geiger et al. |
| 2006/0058647 | A1 | 3/2006 | Strommer et al. |
| 2006/0178828 | A1 | 8/2006 | Moravec |
| 2006/0184016 | A1 | 8/2006 | Glossop |
| 2008/0118135 | A1 | 5/2008 | Averbuch et al. |
| 2008/0281189 | A1 | 11/2008 | Komuro et al. |
| 2009/0227861 | A1 | 9/2009 | Ganatra et al. |
| 2010/0041949 | A1 | 2/2010 | Tolkowsky |
| 2011/0093243 | A1 | 4/2011 | Tawhai et al. |
| 2015/0073266 | A1 | 3/2015 | Brannan et al. |
| 2015/0141858 | A1 | 5/2015 | Razavi et al. |
| 2016/0228038 | A1 | 8/2016 | Stone |
| 2017/0156685 | A1* | 6/2017 | Dickhans ............... A61B 34/20 |

FOREIGN PATENT DOCUMENTS

| | | |
|---|---|---|
| EP | 1929956 A2 | 6/2008 |
| JP | 2007125179 A | 5/2007 |
| WO | 2008111070 A2 | 9/2008 |
| WO | 2009023801 A1 | 2/2009 |
| WO | 2009064715 A1 | 5/2009 |

OTHER PUBLICATIONS

European Search Report from corresponding application No. EP 10 16 2897 dated Apr. 29, 2015.
European Office Action for EP 10 162 897.2 dated Dec. 7, 2015.
European Examination Report for EP 10 162 897.2 dated May 27, 2016.
European Office Action issued in corresponding application No. EP 10 162 897.2 dated Jan. 31, 2017.
Extended European Search Report issued in corresponding European Application No. 18188673.0 dated Nov. 27, 2018, 8 pages.
International Search Report and Written Opinion of the International Searching Authority issued in corresponding Appl. No. PCT/US2018/064954 dated Apr. 1, 2019 (11 pages).

* cited by examiner

SYSTEMS, METHODS, AND COMPUTER-READABLE MEDIA OF ESTIMATING THORACIC CAVITY MOVEMENT DURING RESPIRATION

CROSS REFERENCE TO RELATED APPLICATION

The present application claims the benefit of and priority to U.S. Provisional Application Ser. No. 62/597,200, filed on Dec. 11, 2017 the entire contents of which are incorporated herein by reference.

BACKGROUND

Technical Field

The present disclosure relates to devices, systems, methods, and computer-readable media for estimating tissue movement in, on, and throughout the thoracic cavity during respiration based on detected sensor movement. In particular, the present disclosure relates to devices, systems, methods, and computer-readable media for generating and updating three-dimensional (3D) models of the thoracic cavity as well as for structures within the thoracic cavity, the entirety of which moves during the respiratory cycle.

Description of Related Art

Systems have been developed that enable the generation of 3D models of airways and other luminal networks in a patient's body, typically from a series of computed tomography (CT) images. One such system has been developed as part of the ILOGIC® ELECTROMAGNETIC NAVIGATION BRONCHOSCOPY® (ENB™), system currently sold by Medtronic PLC. The details of such a system are described in commonly-assigned U.S. Patent Appl. Publ. No. 2016/0000302, filed on Jun. 29, 2015, by Brown et al., entitled "SYSTEM AND METHOD FOR NAVIGATING WITHIN THE LUNG," as well as U.S. Pat. No. 9,459,770, entitled "PATHWAY PLANNING SYSTEM AND METHOD," filed on Mar. 15, 2013, by Baker et al., the entire contents of each of which are incorporated herein by reference. While the systems described in U.S. Patent Appl. Publ. No. 2016/0000302 and U.S. Pat. No. 9,459,770 are quite capable, there is always a need for development of improvements and additions to such systems.

SUMMARY

Provided in accordance with embodiments of the present disclosure are systems for visualizing movement of structures within a patient's chest.

In an aspect of the present disclosure, an exemplary system includes an electromagnetic (EM) tracking system including an EM field generator configured to generate an EM field, a plurality of EM sensors attached to a patient and movable within the EM field, and a tracking module configured to detect positions of the plurality of EM sensors within the EM field. The system further includes a display device, and a computing device including a processor and a memory storing instructions which, when executed by the processor, cause the computing device to receive a plurality of images of the patient's chest, generate a first 3D model of an interior of the patient's chest based on the plurality of images of the patient's chest, determine positions of the plurality of EM sensors at full-breath hold, determine positions of the plurality of EM sensors at maximum tidal volume, determine differences between the positions of the plurality of EM sensors at maximum tidal volume and the positions of the plurality of EM sensors at full-breath hold, generate a second 3D model at maximum tidal volume based on the differences between the positions of the plurality of EM sensors at maximum tidal volume and the positions of the plurality of EM sensors at full-breath hold, and cause the display device to display the second 3D model.

In another aspect of the present disclosure, the instructions, when executed by the processor, further cause the computing device to determine positions of the plurality of EM sensors at minimum tidal volume, determine differences between the positions of the plurality of EM sensors at minimum tidal volume and the positions of the plurality of EM sensors at maximum tidal volume, and generate a third 3D model at minimum tidal volume based on the differences between the positions of the plurality of EM sensors at minimum tidal volume and the positions of the plurality of EM sensors at maximum tidal volume.

In yet a further aspect of the present disclosure, the instructions, when executed by the processor, further cause the computing device to select a subset of EM sensors from the plurality of EM sensors, the subset of EM sensors corresponding to a region of the patient's chest, determine current positions of the subset of EM sensors, determine differences between the current positions of the subset of EM sensors and the positions of the subset of EM sensors during maximum tidal volume, minimum tidal volume, and the selected first position of the plurality of EM sensors, and cause the display device to display one of the second, third, or fourth 3D models based on the determined differences between the current positions of the subset of EM sensors and the positions of the subset of EM sensors during maximum tidal volume, minimum tidal volume, and the selected first position of the plurality of EM sensors.

In another aspect of the present disclosure, the instructions, when executed by the processor, further cause the computing device to determine current positions of the plurality of EM sensors, determine differences between the current positions of the plurality of EM sensors and the positions of the plurality of EM sensors at maximum tidal volume or the positions of the plurality of EM sensors at minimum tidal volume, determine that differences between the current positions of the plurality of EM sensors and the positions of the plurality of EM sensors at maximum tidal volume is less than the differences between the positions of the plurality of EM sensors at full-breath hold and the positions of the plurality of EM sensors at maximum tidal volume, or that differences between the current positions of the plurality of EM sensors and the positions of the plurality of EM sensors at minimum tidal volume is greater than the differences between the positions of the plurality of EM sensors at full-breath hold and the positions of the plurality of EM sensors at minimum tidal volume, and generate a fifth 3D model based on the differences between the current positions of the plurality of EM sensors and the positions of the plurality of EM sensors at maximum tidal volume or the positions of the plurality of EM sensors at minimum tidal volume.

In yet another aspect of the present disclosure, the instructions, when executed by the processor, further cause the computing device to determine intra-procedure positions of the plurality of EM sensors at a predetermined interval during a surgical procedure, and determine whether the intra-procedure positions of the plurality of EM sensors exceed the positions of the plurality of EM sensors at minimum tidal volume or the positions of EM sensors at maximum tidal volume.

In a further aspect of the present disclosure, the instructions, when executed by the processor, further cause the computing device to select a 3D model corresponding to the intra-procedure positions of the plurality of EM sensors, when it is determined that the intra-procedure positions of the plurality of EM sensors do not exceed the positions of the plurality of EM sensors at minimum tidal volume and the positions of EM sensors at maximum tidal volume.

In another aspect of the present disclosure, the instructions, when executed by the processor, further cause the computing device to generate a new 3D model at maximum tidal volume or a new 3D model at minimum tidal volume, when it is determined that the intra-procedure positions of the plurality of EM sensors exceed the positions of the plurality of EM sensors at minimum tidal volume or the positions of the plurality of EM sensors at maximum tidal volume.

In yet another aspect of the present disclosure, the instructions, when executed by the processor, further cause the computing device to provide an alert when it is determined that the intra-procedure positions of the plurality of EM sensors exceed the positions of the plurality of EM sensors at minimum tidal volume or the positions of the plurality of EM sensors at maximum tidal volume.

In still another aspect of the present disclosure, the plurality of images of the patient's chest are obtained during a full-breath hold CT scan.

Provided in accordance with embodiments of the present disclosure are methods for visualizing movement of structures within a patient's chest.

In an aspect of the present disclosure, an exemplary method includes receiving a plurality of images of a patient's chest, tracking positions of a plurality of electromagnetic (EM) sensors attached to the patient and movable within an EM field generated by an EM field generator, generating a first 3D model of an interior of the patient's chest based on the plurality of images of the patient's chest, determining positions of a plurality of EM sensors at full-breath hold, determining positions of the plurality of EM sensors at maximum tidal volume, determining differences between the positions of the plurality of EM sensors at maximum tidal volume and the positions of the plurality of EM sensors at full-breath hold, generating a second 3D model at maximum tidal volume based on the differences between the positions of the plurality of EM sensors at maximum tidal volume and the positions of the plurality of EM sensors at full-breath hold, and displaying the second 3D model.

In another aspect of the present disclosure, the method further includes determining positions of the plurality of EM sensors at minimum tidal volume, determining differences between the positions of the plurality of EM sensors at minimum tidal volume and the positions of the plurality of EM sensors at maximum tidal volume, and generating a third 3D model at minimum tidal volume based on the differences between the positions of the plurality of EM sensors at minimum tidal volume and the positions of the plurality of EM sensors at maximum tidal volume.

In a further aspect of the present disclosure, the method further includes selecting a subset of EM sensors from the plurality of EM sensors, the subset of EM sensors corresponding to a region of the patient's chest, determining current positions of the subset of EM sensors, determining differences between the current positions of the subset of EM sensors and the positions of the subset of EM sensors during maximum tidal volume, minimum tidal volume, and the selected first position of the plurality of EM sensors, and displaying one of the second, third, or fourth 3D models based on the determined differences between the current positions of the subset of EM sensors and the positions of the subset of EM sensors during maximum tidal volume, minimum tidal volume, and the selected first position of the plurality of EM sensors.

In yet a further aspect of the present disclosure, the method further includes determining current positions of the plurality of EM sensors, determining differences between the current positions of the plurality of EM sensors and the positions of the plurality of EM sensors at maximum tidal volume or the positions of the plurality of EM sensors at minimum tidal volume, determining that differences between the current positions of the plurality of EM sensors and the positions of the plurality of EM sensors at maximum tidal volume is less than the differences between the positions of the plurality of EM sensors at full-breath hold and the positions of the plurality of EM sensors at maximum tidal volume, or that differences between the current positions of the plurality of EM sensors and the positions of the plurality of EM sensors at minimum tidal volume is greater than the differences between the positions of the plurality of EM sensors at full-breath hold and the positions of the plurality of EM sensors at minimum tidal volume, and generating a fifth 3D model based on the differences between the current positions of the plurality of EM sensors and the positions of the plurality of EM sensors at maximum tidal volume or the positions of the plurality of EM sensors at minimum tidal volume.

In another aspect of the present disclosure, the method further includes determining intra-procedure positions of the plurality of EM sensors at a predetermined interval during a surgical procedure, and determining whether the intra-procedure positions of the plurality of EM sensors exceed the positions of the plurality of EM sensors at minimum tidal volume or the positions of EM sensors at maximum tidal volume.

In yet another aspect of the present disclosure, the method further includes selecting a 3D model corresponding to the intra-procedure positions of the plurality of EM sensors, when it is determined that the intra-procedure positions of the plurality of EM sensors do not exceed the positions of the plurality of EM sensors at minimum tidal volume and the positions of EM sensors at maximum tidal volume.

In a further aspect of the present disclosure, the method further includes generating a new 3D model at maximum tidal volume or a new 3D model at minimum tidal volume, when it is determined that the intra-procedure positions of the plurality of EM sensors exceed the positions of the plurality of EM sensors at minimum tidal volume or the positions of the plurality of EM sensors at maximum tidal volume.

In another aspect of the present disclosure, the method further includes providing an alert, when it is determined that the intra-procedure positions of the plurality of EM sensors exceed the positions of the plurality of EM sensors at minimum tidal volume or the positions of the plurality of EM sensors at maximum tidal volume.

In yet another aspect of the present disclosure, the plurality of images of the patient's chest are obtained during a full-breath hold CT scan.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein.

DETAILED DESCRIPTION

Figure 1:
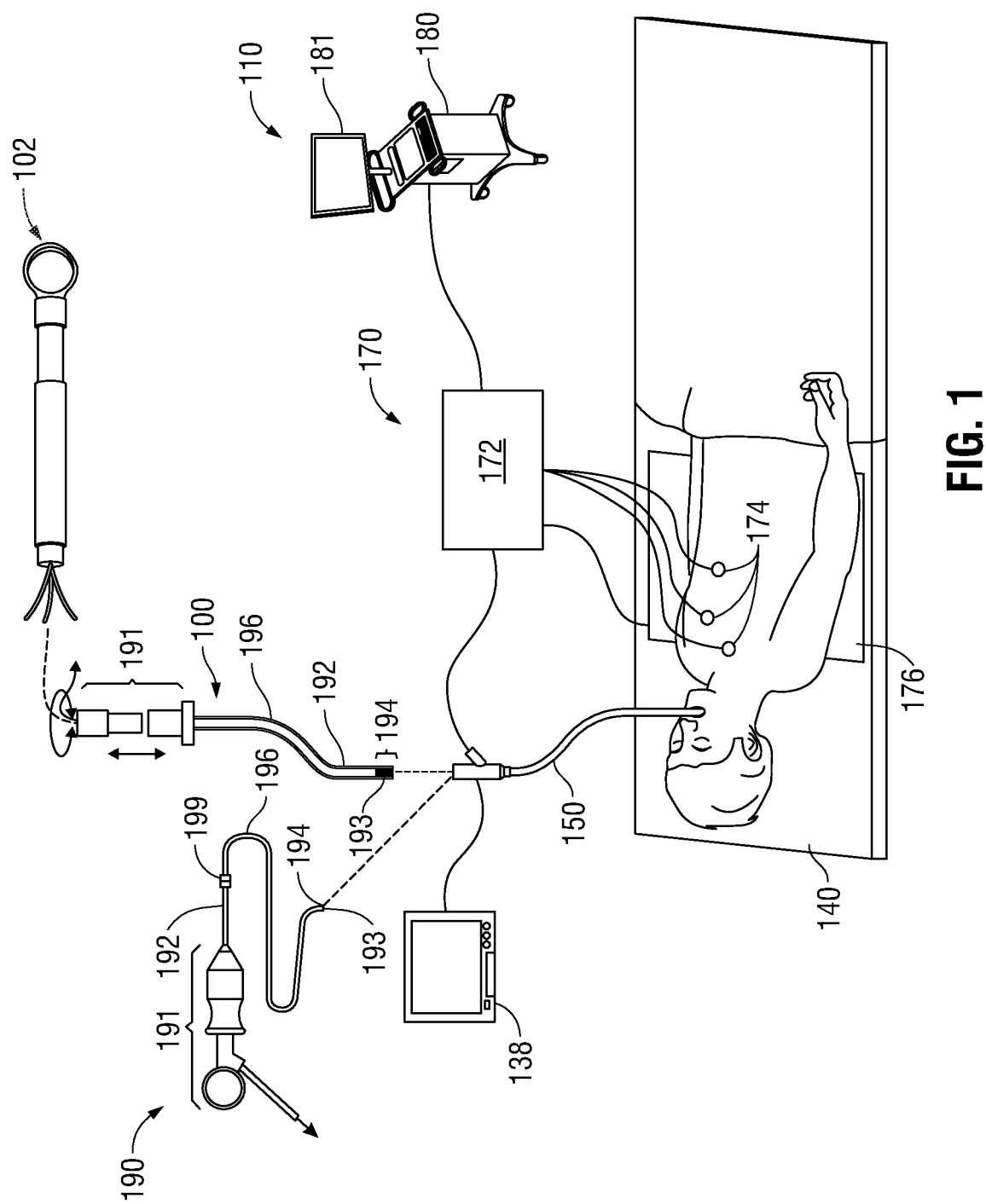
FIG. 1 is a perspective view of an electromagnetic navigation system, in accordance with the present disclosure.

A patient's thoracic cavity and the various structures included therein, adjacent thereto, and/or otherwise associated therewith, moves throughout the patient's respiratory cycle due to inflation and deflation of the patient's lungs. For example, during the patient's respiratory cycle, the lungs, and in particular the bronchioles and alveoli, expand and contract. Though individually small, the compound effect of such expansion and contraction results in significant movement for the entirety of the lungs and the airways, as well as other structures within the patient's chest. The amount that the patient's lungs inflate and deflate may be indicative of the patient's respiratory health. Various tests, such as the pulmonary function test (PFT), cardiopulmonary exercise test (CPET), and/or methacholine challenge test, among others, may be performed on the patient to assess the patient's respiratory health (such tests are referred to hereinafter as "respiratory tests"). While it is helpful in various of these tests to measure the difference in volume or flow rates of air of the patient's lungs and chest when fully inhaling and fully exhaling to determine the patient's lung capacity and function, this alone does not provide a complete picture of the patient's respiratory health. For example, differences in lung flow rates or capacity over time and/or before and after treatment may be indicative of improvement or deterioration of the patient's respiratory health, but lung capacity or flow does not give any indication of movement of the chest or the structures within the patient's chest during respiration.

Described hereinbelow are various embodiments of systems and methods for assessing a patient's respiratory health. In embodiments, sensors (for example displacement sensors) are attached to the patient's chest and/or back prior to the start of a respiratory assessment or a respiratory test. The patient may then be instructed to breath normally, fully inhale, fully exhale, cough, sigh, perform various physical activities, and/or be given medication or other treatment(s) (depending on the requirements of the test). Further, the patient may be positioned in various manners or orientations during the respiratory assessment or respiratory test, for example, the patient may be positioned in a supine, seated, and/or standing position, in addition to the traditional position of lying flat on the patient's back. The positions of the sensors are then tracked during the patient's respiratory cycle to determine displacement of the sensors as the patient's chest moves. The positions of these sensors may be evaluated collectively (e.g. all sensors together), as a subset (e.g. particular groups of sensors defining a region may be evaluated separately), and/or individually. As such, data may be collected regarding movement of the patient's chest as a whole, as well as various locations or portions of the patient's chest that may be moving separately and/or uncorrelated to other locations or portions. Data collected prior to the start of a respiratory assessment, respiratory test, or treatment may serve as a baseline measurement, and may later be compared with data collected during and/or after a respiratory assessment, respiratory test, or treatment to determine changes in the patient's respiratory cycle and/or breathing capacity, as further described below.

As referred to herein, a location of a sensor is the place on the patient's body where the sensor is attached. The location of the sensor remains the same throughout the respiratory test. A position of a sensor is the position within three-dimensional space of the sensor relative to a point from which displacement of the sensor is measured. For example, the position of the sensor may be tracked relative to a base board placed under the patient and/or another sensor attached to the patient's body. Thus, the position of the sensor is expected to change during the patient's respiratory cycle.

In some embodiments, images are also taken of the patient prior to and/or during the respiratory test. For example, photographic or videographic images of the patient's chest may be captured during the patient's respiratory cycle to visually detect movement of the patient's chest during respiration. In addition, the images may be processed by a computing device to generate a model of the patient's chest and/or to identify the locations of the sensors on the patient's chest and/or back. The movement of the sensors, as they are displaced during the patient's respiratory cycle, are then correlated to the locations on the patient's chest and/or back where the sensors are attached, and an inference may then be made regarding movement of structures within the patient's chest underlying the locations where the sensors are attached. In other embodiments, the sensors are attached to predetermined locations on the patient's chest and/or back. For example, one or more sensors may be attached to the patient's skin approximately at the inferior border of the patient's sternum, and one or more sensors may be attached to the patient's skin on the patient's spine approximately at the T5 vertebra. Additionally or alternatively, one or more sensors may be attached to the patient's skin in the supraclavicular region bilaterally, and/or one or more sensors may be attached to the patient's skin about a mid-axillary line at the level of the patient's $12^{th}$ rib. In such embodiments, the locations of the sensors relative to the patient's body are known, and thus need not be identified via image processing.

In further embodiments, radiographic images of one or more portions of the patient's body may be obtained prior to and/or during the respiratory test. The radiographic images may be obtained using computed tomography (CT), magnetic resonance imaging (MRI), positron emission tomography (PET), cone-beam computed tomography (CBCT), X-ray, fluoroscopy, and/or any other relevant imaging modality known to those skilled in the art. As described further below, the radiographic images may be processed by a computing device to identify various structures inside the patient's body, including the pulmonary system (e.g. the lungs, airways, and pleura), cardiovascular system (e.g. the heart and blood vessels), lymphatic system (e.g. lymph nodes and ducts), ribs, as well as other organs and structures, and further detect how the various structures move relative to each other. One or more models, such as a three-dimensional (3D) model of the structures in the patient's chest, may then be generated based on the radiographic images and the structures identified therein. Additionally, one or more 3D models may be generated based on radiographic images obtained at different points and/or during different phases of the patient's respiratory cycle. The positions of the sensors at the time that the radiographic images are obtained may be determined and positions of structures within the patient's chest may then be associated with those positions of the sensors, and the corresponding point in the patient's respiratory cycle. Thus, by obtaining radiographic images and tracking the positions of the sensors at various points and during various phases of the patient's respiratory cycle, relative positions (and thus movement) of the structures within the patient's chest may similarly be determined and tracked throughout the patient's respiratory cycle. Further, after the positions of the structures have been determined at sufficient points during the patient's respiratory cycle, a dynamic model or simulation may be generated by interpolating the positions of the various structures at different points during the patient's respiratory cycle and simulating smooth movement of those structures (and the thoracic cavity as a whole) between the various positions. An actual or simulated (if a measured position is not available for a particular point) position of the various structures in the patient's chest may then be determined for all points and phases of the patient's respiratory cycle to give greater insight into the patient's respiratory health than can be attained as opposed to merely measuring lung capacity or flow.

Further, several recognized variances from the typical respiratory cycle, such as yawning, coughing, sneezing, sighing, and/or vascular and cardiac pulsations may all contribute to movement of the lungs, one or more portions of the lungs, and/or one or more structures within the lungs within the thoracic cavity, and may be detected, analyzed, and simulated by using the above-described dynamic 3D modeling technique. These variations in the positions of various structures within the patient's chest may cause changes within the lungs that may not be represented in a 3D model generated from a single set of radiographic image data given that the radiographic imaging generate a fairly static set of images at a particular point (often at full breath hold) in the respiratory cycle.

In addition to the patient-specific models described above, generic models of expected movement of structures within a patient's chest generated based on data assembled from a variety of patients, and particular, patient's having similar medical characteristics. For example, one or more generic models simulating movement of structures in various parts of patients' chests during various phases of the patients' respiratory cycle may be generated based on patterns determined from data points (such as the positions of the structures) collected from radiographic images of the various patients. Over time, as more data points are collected, the generic models may be further focused on particular patient conditions, such as age, gender, body type, physical condition, medical condition, disease progression, and prior treatment history. One or more of the generic models may then be used to simulate expected movement of structures within a particular patient's chest even if radiographic images have not been obtained for that patient.

Knowing the positions and relative movement of the various structures within the patient's chest at various points and during various phases of the patient's respiratory cycle may be useful in diagnosing various respiratory conditions and/or diseases affecting the lungs. For example, in addition to initial diagnosis of a condition and/or disease, the movement of structures within the patient's chest observed after treatment and/or medical or surgical intervention may be compared with data observed prior to the treatment or intervention to determine progression and/or improvement in the condition and/or disease. Additionally, knowing the positions and relative movement of the various structures within the patient's chest at various points of the patient's respiratory cycle may assist a clinician in accurately performing various diagnostic and/or treatment procedures (for example biopsy, tissue ablation, resection, etc.) within the patient's chest and reduce risk of injury to critical structures proximate a treatment site. Further benefits of the above-described 3D modeling techniques include detecting whether the lungs oppose the chest wall and/or if there is pleural fluid between the lung and the chest wall, as well as determining how these and other conditions affect movement of structures in the patient's chest during the patient's respiratory cycle.

As noted above, and described in greater detail below, sensors may be placed on the patient's chest, and movement (such as displacement) of such sensors may be detected as the patient breathes. Baseline measurements may be taken to determine an amount of displacement during various phases of the patient's respiratory cycle, i.e. maximum inhalation, maximum exhalation, maximum tidal volume, minimal tidal volume, and/or other maneuvers, etc. Based on such measurements, a variety of different assessments may be performed, such as to determine a maximum inspiratory capacity and a residual volume of the patient's lungs, as well as to assess a response to any intervention in the chest or lungs whether it be medical, such as with inhaled or oral medications, or procedural, such bronchoscopy, surgery, image-guided procedures, etc. Further, the systems and methods described herein may also be used to produce a baseline set of measures relative to a patient's breathing pattern, with or without underlying lung disease, such that, should an exacerbation of underlying disease occur, any deviation from the baseline can be assessed and any response to potential therapy tracked relative to this baseline. Such measurements and observations would allow for assessments of the patient's health and particularly the patient's breathing capacity.

While the above-described assessments and observations may be performed without requiring further medical or surgical intervention, these assessments and observations may also form part of a diagnostic and/or treatment procedure, such as a minimally invasive electromagnetic navigation (EMN) procedure. EMN generally involves at least two phases: (1) planning a pathway to a target located within, or adjacent to, the patient's airways; and (2) navigating one or more tools to a region of interest along the planned pathway. These phases are generally referred to as (1) "planning" and (2) "navigation." Prior to the planning phase, the patient's lungs are imaged by, for example, a CT scan, although additional applicable methods of imaging will be known to those skilled in the art. The image data obtained during the CT scan may then be stored in, for example, the Digital Imaging and Communications in Medicine (DICOM) format, although additional applicable formats will be known to those skilled in the art. The CT image data may later be loaded into a planning software application ("application")

to be used during the planning phase of the EMN procedure. The images obtained during the CT scan may be obtained during one or more phases of the patient's respiratory cycle. For example, a full-breath hold CT scan may be performed while the patient has inhaled deeply and held his or her breath. Additional CT scans may be performed maximum exhalation, normal tidal volume breathing, and/or various other points during the patient's respiratory cycle. One or more 3D models may then be generated based on the CT image data. Such 3D models are a representation of the thoracic cavity, and its contents (e.g., lungs, blood vessels, etc.) while the patient is at full-breath hold, or any other point during the patient's respiratory cycle at which the CT scan was performed. CT scans are typically performed at full-breath hold, and the movement of structures within the patient's chest associated with the change from full-breath hold to tidal volume breathing can be significant. Systems and methods to compensate for these changes between a 3D model generated at full-breath hold and the physiology experienced by the clinician as the patient undergoes routine or tidal volume breathing is one aspect of the present disclosure. Specifically, the present disclosure utilizes detected sensor positions, obtained prior to and during the EMN procedure, to generate both static and dynamic 3D models based on actual and/or interpolated (simulated) data points to represent the full range of the patient's respiratory cycle, and display the 3D models during the EMN procedure such that the clinician need not seek to compensate for the differences in locations between a static 3D model generated at full-breath hold and the locations of airways and targets during tidal volume breathing.

With reference to FIG. 1, an EMN system 110 is depicted in accordance with the present disclosure. One such EMN system is the SuperDimension® ENB™ system currently sold by Medtronic PLC. While the description below uses EMN system 110 as an illustrative embodiment, those skilled in the art will recognize that the methods described below may be performed using various other surgical intervention systems, or may even partially be performed without using such systems. In particular, as noted above, various aspects of the present disclosure require merely a system for tracking sensors attached to a patient's chest and/or back, and generating one or more models based on the tracked positions of such sensors. Additionally, while EMN system 110 described hereinbelow includes an electromagnetic tracking system and associated electromagnetic sensors for detecting displacement of the patient's chest during the patient's respiratory cycle, those skilled in the art will appreciate that various other types of sensors and tracking systems may be used to monitor movement of the patient's chest without departing from the scope of the present disclosure. Further, EMN system 110, as shown in FIG. 1, depicts a patient lying on his or her back during an EMN procedure. However, those skilled in the art will appreciate that various aspects of the methods described below may be performed on a patient positioned in various other positions and/or orientations, including supine, seated, and/or standing up. As such, the embodiments described below are provided merely for illustrative purposes, and are not intended to limit the scope of the present disclosure. Further, while the below-described EMN system 110 uses CT as an illustrative radiographic imaging modality, those skilled in the art will recognize that various other imaging modalities, for example the modalities described above, may be used instead of and/or in combination with CT without departing from the scope of the present disclosure.

EMN system 110 generally includes an operating table 140 configured to support a patient; a bronchoscope 150 configured for insertion through the patient's mouth and/or nose into the patient's airways; monitoring equipment 160 coupled to bronchoscope 150 for displaying video images received from bronchoscope 150; a tracking system 170 including a tracking module 172, a plurality of reference sensors 174, an electromagnetic field generator 176; and a computing device 180 including software and/or hardware used to facilitate pathway planning, identification of the region of interest, navigation to the region of interest, and performing one or more diagnostic and/or treatment procedures at the region of interest.

FIG. 1 also depicts two types of catheter guide assemblies 100, 190. Both catheter guide assemblies 100, 190 are usable with EMN system 110 and share a number of common components. Each catheter guide assembly 100, 190 include a handle 191, which is connected to an extended working channel (EWC) 196. EWC 196 is sized for placement into the working channel of a bronchoscope 150. In operation, a locatable guide 192, including an electromagnetic (EM) sensor 194, is inserted into EWC 196 and locked into position such that EM sensor 194 extends a desired distance beyond distal tip 193 of EWC 196. The position of the EM sensor 194, and therefore distal tip 193 of EWC 196, within an electromagnetic field generated by the electromagnetic field generator 176, can be derived by the tracking module 172, and computing device 180.

Reference sensors 174 may be attached to various locations on the patient's chest and/or back, such as the above-described predetermined locations. In embodiments of the present disclosure, reference sensors 174 may serve at least two purposes: (1) to define a frame of reference, in combination with EM field generator 176, for tracking of EM sensor 194 within the EM field generated by EM field generator 176, and (2) to monitor movement of the patient's chest during the patient's respiratory cycle as determined based on displacement of reference sensors 174 relative to EM field generator 176. Thus, reference sensors 174, in combination with CT image data of the patient's chest obtained prior to and/or during the EMN procedure, may be used to determine a current point and/or phase of the patient's respiratory cycle, and thereby determine the relative positions of structures within the patient's chest.

As illustrated in FIG. 1, the patient is shown lying on operating table 140 with bronchoscope 150 inserted through the patient's mouth and into the patient's airways. Bronchoscope 150 includes a source of illumination and a video imaging system (not shown) and is coupled to monitoring equipment 160, e.g., a video display, for displaying the video images received from the video imaging system of bronchoscope 150.

As further shown in FIG. 1, electromagnetic field generator 176 is positioned beneath the patient. Electromagnetic field generator 176 and the plurality of reference sensors 174 are interconnected with tracking module 172, which derives the position of each reference sensor 174 in six degrees of freedom. One or more of reference sensors 174 are shown as attached to the patient's chest. The six degrees of freedom coordinates of reference sensors 174 are sent to computing device 180, which includes an application 281, which uses data from reference sensors 174 to calculate a patient coordinate frame of reference.

In addition to using reference sensors 174, EM sensor 194, in conjunction with tracking system 170, also enables tracking of endobronchial tool 102 as the patient breathes during the procedure. Tracking system 170 is configured to determine movement of the airways during the patient's respiratory cycle based on the movement of reference sensors 174, and/or EM sensor 194 included in endobronchial tool 102. Movement of the airways and regions of interest can be asynchronous during respiration. Detection of the actual movement of the airways at a particular location can be compared to the expected location of that portion of the airways as determined by a 3D model corresponding to that point or phase of the patient's respiratory cycle, as determined based on the position of the reference sensors 174, and if outside of a certain tolerance, the clinician may be notified via the user interface. Further, this data may be employed to update the 3D models and/or generate additional 3D models, and may be stored for further use in future 3D models and/or to generate generic 3D models. For example, empirically determined movement of a particular bifurcation (e.g., $3^{rd}$ or $4^{th}$) of the airways may provide useful data for generating 3D models of the patient's chest, as well as for the generic 3D models once sufficient data has been collected and standardized to account for differences in physiology from patient to patient.

In accordance with one embodiment of the present disclosure, reference sensors 174 may be attached to the patient's chest and/or back at predetermined and repeatable locations prior to conducting a CT scan. Once reference sensors 174 are placed, a clinician can request the patient inhale deeply to achieve a lung volume approximately the same as during the CT scan (i.e., full-breath hold). Subsequently, the patient returns to tidal volume breathing. By utilizing the change in positions of reference sensors 174 within the electromagnetic field between full-breath hold and tidal volume breathing, computing device 180 may establish baseline data regarding the movement of the patient's chest during the patient's respiratory cycle. The baseline data may later be used to determine which subsequently-generated 3D model corresponds to the positions of structures within the patient's chest during tidal volume breathing as well as track the patient's respiratory cycle through both normative tidal volume breathing and with such aspects as yawning, coughing, sigh breaths, and the like. Though described herein as being performed before the CT imaging, the procedure above could be performed following the CT imaging, for example as part of a pre-procedure calibration process. In such a scenario, the same or similar reference sensors 174 may be attached to the patient's chest and/or back at the same locations as during the CT scan. Further, to assist in both the 3D model analysis and the attachment of reference sensors 174 following the CT scan, CT compatible surrogates may be placed on the patient during imaging at the locations where reference sensors 174 will be attached. These surrogates appear in the CT image data and may appear in the 3D model, thus providing an additional frame of reference for the clinician as objects that may be used in the data processing to arrive at the 3D model generated by computing device 180.

In a further embodiment, by requesting that the patient perform a full exhalation, a further baseline data set may be acquired from the reference sensors 174. This may be accompanied by a second CT scan at full exhalation. This second CT scan data provides a second CT data set, from which a second 3D model of the lungs may be generated. With the full exhalation and full inhalation data sets, both the minimum and maximum displacement positions of reference sensors 174 are determined, which provides a bounded set of reference sensor 174 positions that may be used to generate simulated and/or dynamic 3D models in accordance with the detected positions of reference sensors 174 at any point therebetween, as further described in the detailed description of FIG. 3. Additionally, one or more intermediate measurements of the displacement of reference sensors 174 and corresponding CT scans may be obtained either pre-procedurally and/or intra-procedurally to provide additional data points regarding intermediate changes in the movement of both reference sensors 174 and the structures within the patient's chest throughout the patient's respiratory cycle. By comparing the positions of reference sensors 174 during the tidal volume breathing (as experienced during a procedure) to the positions of reference sensors 174 during the CT scans and/or baseline determinations, the differences may be ascertained and used to determine expected movement of the structures within the patient's chest during the respiratory cycle, as will be described in greater detail below.

Generally, during a CT scan, a single set of image slices (CT image data) is generated. Computing device 180 utilizes the CT image data, or other image data in DICOM format, for generating and displaying a 3D model of the patient's airways. The 3D model and image data derived from the 3D model enables the identification of the region of interest (automatically, semi-automatically or manually), and allows for the selection of a pathway through the patient's airways to the region of interest. More specifically, the CT image data is processed and assembled into a 3D volume, which is then utilized to generate the 3D model of the patient's airways. The 3D model may be presented on a display monitor 181 associated with computing device 180, or in any other suitable fashion. Using computing device 180, various slices of the 3D volume and views of the 3D model may be presented and/or may be manipulated by a clinician to facilitate identification of the region of interest and selection of a suitable pathway through the patient's airways to access the region of interest. The 3D model may also show marks of the locations where previous procedures were performed. These marks may also be selected as the region of interest to which a pathway can be planned. Once selected, the pathway is saved for use during the navigation phase of the EMN procedure. As noted above, this CT scan is usually performed at full-breath hold (i.e., maximum inhalation and expansion of the lungs and thoracic cavity). However, additional CT scans, for example, at maximum exhalation, and/or various points in between maximum inhalation and maximum exhalation, may be performed and data obtained during such additional CT scans may be used to determine movement of the patient's lungs and structures therein to generate additional 3D models based on the various points or phases of the patient's breathing cycle.

Further, as noted above, while the above description of EMN system 110 involves preparing for and/or performing an ENB diagnostic and/or treatment procedure, it is also envisioned that generation of the 3D models of the patient's lungs may occur separate from an ENB diagnostic or treatment procedure and separate from any imaging. In such embodiments, reference sensors 174 may be attached to the patient's chest and/or back in a variety of different positions and under a variety of different conditions both at rest and with exercise. A specific example is when a patient is lying on table 140, and measurements of the displacement of reference sensors 174 during maximum inhalation, maximum exhalation, and/or regular tidal volume breathing may be collected and tracked dynamically to determine expansion and contraction of the patient's chest and/or movement of the structures therein. Assessments of the patient's health and breathing capacity may then be made based on such measurements of displacement of reference sensors 174 as well as with respect to a dynamic assessment relative to any given state of the patient whether at baseline or with exercise, etc. For example, a patient's breathing capacity may be tracked over time, and effects of medication and/or treatments performed on the patient may be determined based on changes in the patient's breathing capacity, and/or respiratory function, etc.

Figure 2:
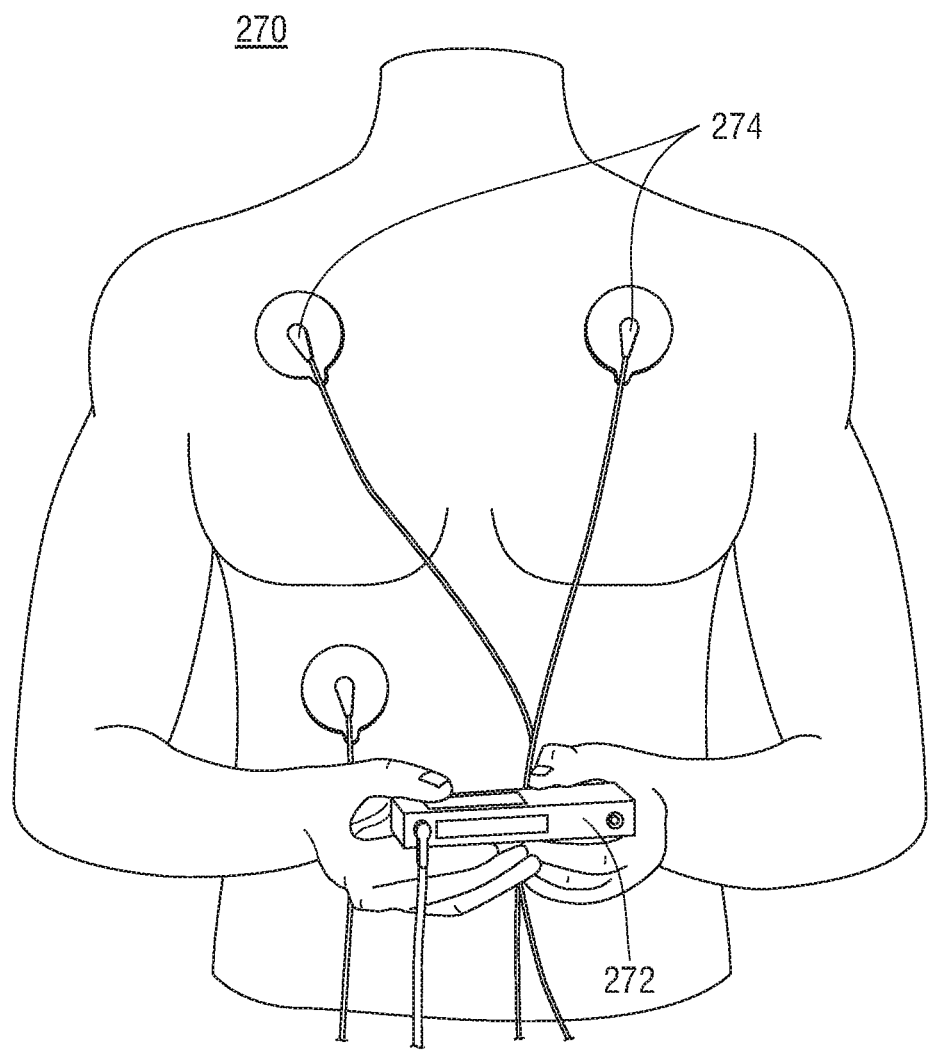
FIG. 2 is a diagram of a system 270 for determining movement of a patient's chest during the patient's respiratory cycle, in accordance with the present disclosure.

With reference to FIG. 2, there is shown diagram of a system 270 for determining movement of a patient's chest during the patient's respiratory cycle, in accordance with embodiments of the present disclosure. System 270 includes a plurality of displacement sensors 274 attached to predetermined locations of a patient's chest and/or back. Displacement sensors 274 are coupled to a tracking system 272 configured to determine displacement of displacement sensors 274. In embodiments, at least one reference sensor (not shown) and/or a sensor board (not shown) are also attached to the patient's body. Tracking system 272 may determine the displacement of displacement sensors 274 in relation to the reference sensor and/or the sensor board. Displacement sensors 274 may be EM sensors similar to EM sensors 174 and/or any other type of sensor usable to determine movement of the patient's chest. System 270 may be usable to track movement of the patient's chest during various activities and in various positions, as described above. Additionally, system 270 may be used in conjunction with EM system 110 during performance of the EMN procedure described above.

Figure 3:
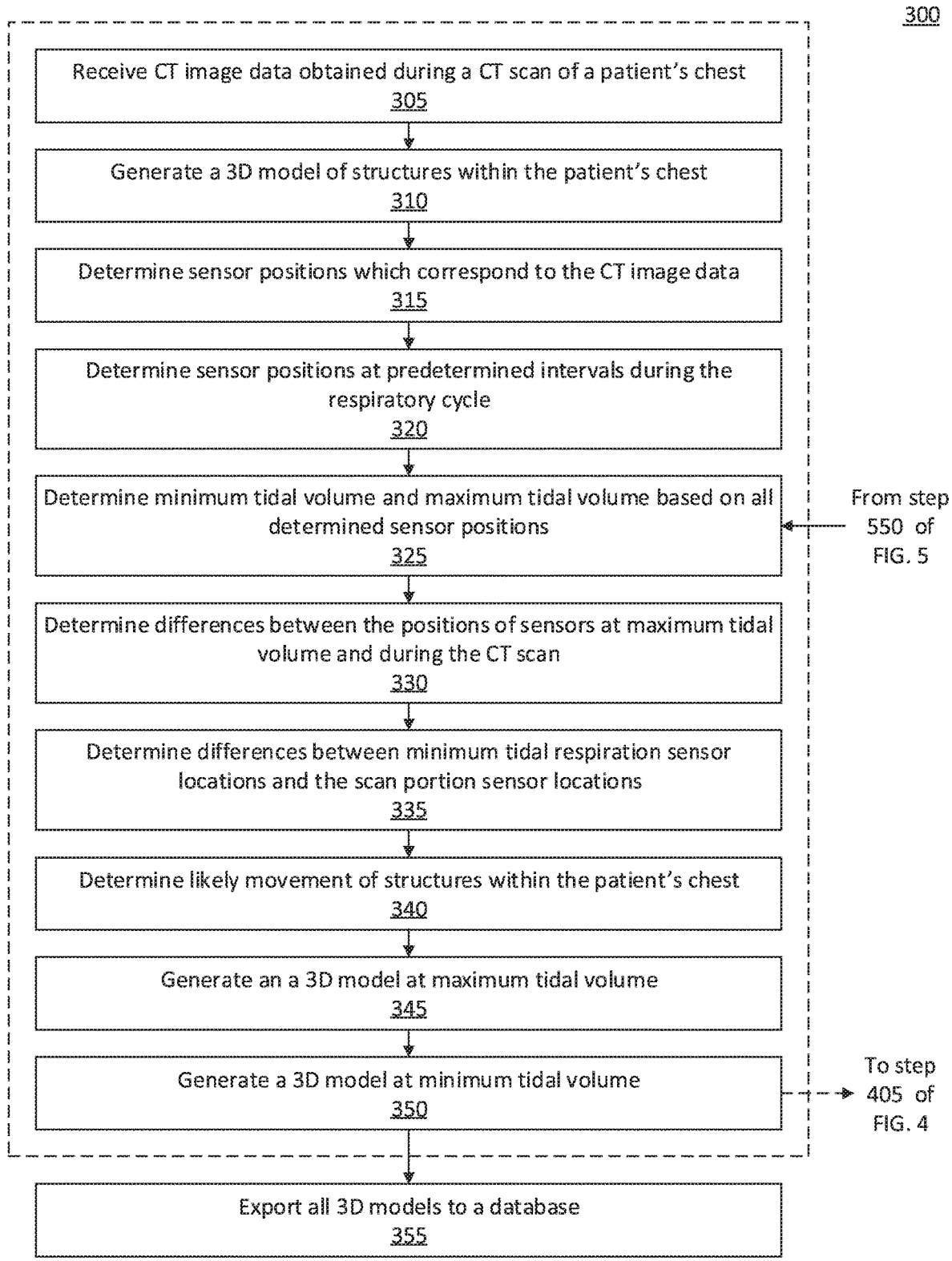
FIG. 3 is flowchart of example method for pre-procedure 3D model generation based on the positions of a plurality of reference sensors, in accordance with the present disclosure.

Referring now to FIG. 3, there is shown a flowchart of an illustrative method 300 for generating a pre-procedure 3D model in accordance with embodiments of the present disclosure. Method 300 begins at step 305, where computing device 180 receives CT image data 214 obtained during a pre-procedure CT scan of the patient's chest while the patient was at a particular phase of the respiratory cycle (e.g., full-breath hold). CT image data 214 may be received from memory 202, or externally via network interface 208. Next, at step 310, computing device 180, such as via processor 204, generates a 3D model of structures within the patient's chest based on CT image data 214. Next, at step 315, after the patient is positioned on an operating table 140 having an EM field generator 176 and with reference sensors 174 attached to the patient's chest and/or back, the patient is asked to recreate the breathing condition of the CT scan (e.g., full-breath hold), and the positions of reference sensors 174 in the EM field at the same point or phase of the patient's breathing cycle as the pre-procedure CT scan is determined.

Next, at step 320, with the patient reference sensors 174 attached, the patient is asked to breathe normally (e.g., tidal volume breathing). Processor 204, at predetermined intervals (e.g., a function of a clock associated with processor 204) during the patient's respiratory cycle, may determine the positions of reference sensors 174. For example, at every 0.1, 0.25, 0.5 or 1-second, processor 204 may determine the positions of reference sensors 174 and store the positions in memory 202 and/or database 215. Next, at step 325, processor 204 determines the maximum and minimum tidal volume positions of reference sensors 174 based on the detected positions of reference sensors 174 determined at the predetermined intervals. This may require multiple breathing cycles to ensure that the actual minimum and maximum are recorded. In addition, the patient may be asked to cough, sigh, yawn, or produce other respiratory maneuvers that can be recorded, assessed and logged into the system. The positions of reference sensors 174 may be evaluated collectively, individually, and/or in various subsets or groups corresponding to particular regions of the patient's chest.

At step 330, the differences between the positions of reference sensors 174 during the pre-procedure CT scan (e.g., full-breath hold) and the positions of reference sensors 174 during tidal volume breathing may be determined. In one example, the differences between the x, y, and z coordinates of reference sensors 174 obtained during full-breath hold and at maximum tidal volume may be determined, such as changes for a particular reference sensor 174 equaling 1 millimeters (mm), 2 mm, and 4 mm, for the x, y, and z coordinates respectively. The differences between the positions of reference sensors 174 may be evaluated collectively, individually, and/or in various subsets or groups corresponding to particular regions of the patient's chest, thereby providing data regarding movement of the patient's chest as a whole, as well as localized data regarding particular regions of the patient's chest. Next, at step 335, the differences between the positions of reference sensors 174 during full-breath hold and the positions of reference sensors 174 at minimum tidal volume may be determined. This provides a range of differences between the positions of reference sensors 174 at full-breath hold (i.e., corresponding to the phase of the patients breathing cycle during the CT scan) and during tidal volume breathing. In addition, further data points may be acquired at various other points or phases throughout the respiratory cycle, as described in the detailed description of FIGS. 4A and 4B.

Those skilled in the art will understand that no registration between the 3D model and the patient is necessary at this point as the most relevant data being acquired is the difference in positions of reference sensors 174 between full-breath hold and tidal volume breathing. Thus, the data may be determined either before or after acquisition of the CT image data, as noted above. Further, any alterations in the apposition of the lungs to the chest wall can be recorded and such data stored collectively to determine any changes in static or dynamic function over time as well as to be able to use such data to create a predictive model to assess for and predict areas where there might not be lung apposition to the chest wall.

Next, method 300 proceeds to step 340 where processor 204, using the determined differences from steps 330 and 335, determines the likely movement of the structures within the patient's chest relative to the 3D model generated at step 310 for both maximum tidal volume and minimum tidal volume and to generate one or more simulated or dynamic 3D models. For example, if the determined differences are similar to the example described above of changes for a particular reference sensor 174 equaling 1 mm, 2 mm, and 4 mm, for x, y, and z coordinates respectively, the positions of the structures within the patient's chest as included in the 3D model corresponding to a position at or near the position of the particular reference sensor 174 may be adjusted to account for the changes at maximum tidal volume based on x, y, and z movement of 1 mm, 2 mm, and 4 mm, respectively. Such adjustments may be calculated for each reference sensor 174 and then averaged together, each reference sensor 174 may be evaluated individually, various subsets or groups of reference sensors 174 may be evaluated separately, and/or the change in position for each reference sensor 174 may be weighted such that the detected movement of each reference sensor 174 is applied to the various structures within the patient's chest based on, for example, a distance from reference sensor 174, the type of tissue underlying the position of reference sensors 174, and/or a combination of some or all of these factors and/or other factors affecting movement of the structures within the patient's chest or a particular portion of such structures or the patient's chest itself during respiration.

Next, at steps 345 and 350, intermediate 3D models at maximum tidal volume and minimum tidal volume, respectively, are generated. As noted above, these intermediate 3D models may be simulated and/or dynamic 3D models generated based on the above-described calculations of likely movement of structures within the patient's chest, as opposed to 3D models generated based on CT image data. Optionally, after step 350, method 300 may proceed to step 405 of FIG. 4B, as described below. Thereafter, at step 355, all 3D models are stored in database 215. In addition to the 3D models generated at maximum and minimum tidal volume breathing (steps 345 and 350), one or more 3D models may be generated for additional positions between maximum and minimum and tidal volume breathing, as is further described with reference to FIGS. 4A and 4B below.

Figure 4A:
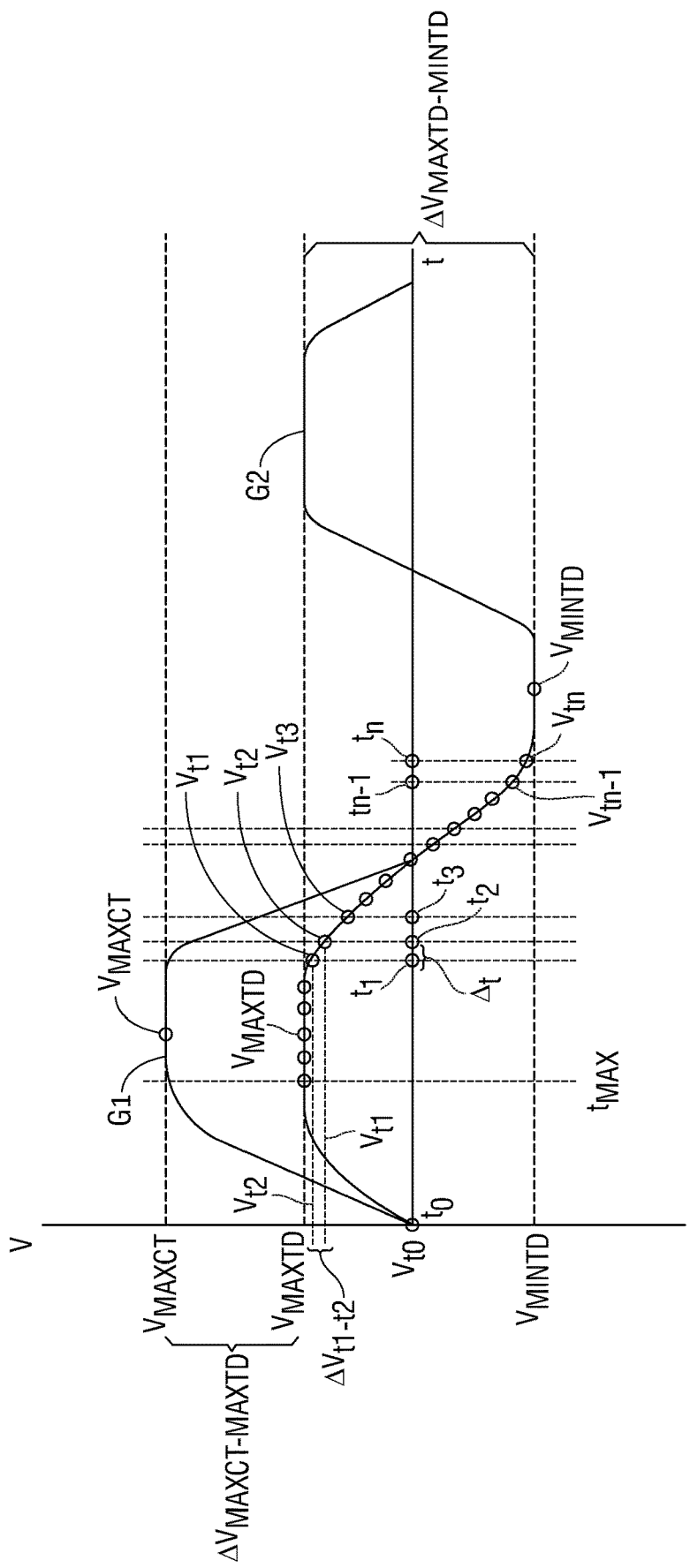
FIG. 4A is a graph illustrating changes in thoracic cavity volume during a CT scan and during respiration, in accordance with the present disclosure.

Referring now to FIG. 4A, there is shown a graph illustrating changes in thoracic cavity volumes. Two graphs G1 and G2 are shown in FIG. 4A and illustrate near-sinusoidal curves. The x-axis corresponds to time t and the y-axis corresponds to volume V of the thoracic cavity. Graph G1 corresponds to a maximum volume during a full-breath hold CT scan and graph G2 corresponds to normal tidal volume breathing observed either pre-procedure, intra-procedure or post-procedure. The changes in volume V also correspond to the movement of reference sensors 174. As detailed herein, during the CT scan, the patient is generally asked to take a deep breath and remain at full-breath hold as the CT scan is performed. The CT scan portion is illustrated in graph G1 from time $t_0$ to time $T_{MAXCT}$ as the volume of the lungs changes from volume $V_{t0}$ to volume $V_{MAXCT}$. As shown in graph G1, the patient slowly inhales and graph G1 ramps upward until reaching volume $V_{MAXCT}$. As described in the detailed description of FIG. 3, positions of reference sensors 174 at volume $V_{MAXCT}$ are determined and a 3D model is generated at volume $V_{MAXCT}$.

Referring now to graph G2, during normal tidal volume breathing observed either pre-procedure or intra-procedure, the volume of the patient's thoracic cavity changes between volume $V_{MAXTD}$, the maximum tidal volume during respiration to volume $V_{MINTD}$, the minimum tidal volume during respiration, with one or more intermediate volumes $V_{tn}$ there between. As detailed herein, during pre-procedure, intra-procedure, or post procedure tidal volume breathing, the patient's thoracic cavity volume is less than volume $V_{MAXCT}$, such that there is a difference $\Delta V_{MAXCT}-V_{MAXTD}$, which is the difference between the volume $V_{MAXCT}$ at full-breath hold and the volume $V_{MAXTD}$ at tidal volume breathing. This difference is also associated with a change in positions of the reference sensors 174.

As described in the detailed description of FIG. 3, the difference $\Delta V_{MAXCT}-V_{MAXTD}$, based on the changes in positions of reference sensors 174 from the full-breath hold CT to the maximum tidal volume breathing, is utilized to generate a 3D model at volume $V_{MAXTD}$. Similarly, using the positions of reference sensors 174 at volume $V_{MAXTD}$ and volume $V_{MINTD}$ and based on the difference $\Delta V_{MAXTD}V_{MINTD}$, the 3D model at volume $V_{MINTD}$ may be generated. Thus, as detailed in FIG. 3, two 3D models, a 3D model at volume $V_{MAXTD}$ and a 3D model at $V_{MINTD}$ are generated.

Utilizing the one or more intermediate volumes $V_{tn}$, each determined at a time interval $\Delta t$, simulated or dynamic 3D models at each volume $V_{tn}$ may be generated by a similar method to that described above. Each intermediate volume $V_{tn}$ may be obtained at $\Delta t$ time intervals from $V_{MAXTD}$ to $V_{MINTD}$. In other embodiments, intermediate volume $V_{tn}$ may be obtained at $\Delta t$ time intervals from $V_{MAXTD}$ through $V_{MINTD}$ and returning to $V_{MAXTD}$. By using the differences between the volumes at different times and the positions of reference sensors 174 at each time, additional 3D models may be generated.

For example, as shown in FIG. 4A, time t1 is the first time t following time $t_{MAX}$ where $V_{MAXTD}$ was determined and the 3D model at $V_{MAXTD}$ was generated. At time t1 the volume is $V_{t1}$. By using the difference between the positions of reference sensors 174 at volume $V_{MAXTD}$ and volume $V_{t1}$, and based on the difference $\Delta V_{MAXTD}-V_{t1}$, a simulated 3D model at volume $V_{t1}$ may be generated based on the 3D model at volume $V_{MAXTD}$. Thus, during the first iteration, a 3D model is generated for volumes $V_{MAXTD}$, $V_{t1}$, and $V_{MINTD}$. Next, at time t2 where the volume is $V_{t2}$, a simulated 3D model is generated. For time t2, by using the difference between the positions of reference sensors 174 at volume $V_{t1}$ and volume $V_{t2}$ and based on the difference $\Delta V_{t1}-V_{t2}$, a simulated 3D model at volume $V_{t2}$ may be generated based on the 3D model at volume Va. This procedure, using the previous 3D model generated to generate a new 3D model, may be utilized n-times, thereby generating n number of 3D models, using the difference between the positions of reference sensors 174 at volume $Vt_{n-1}$ and volume $V_{tn}$. Based on the difference $\Delta V_{tn-1}-V_{tn}$, the 3D model at volume $V_{tn}$ may be generated. In other embodiments, the difference may also be calculated based on the second or third preceding 3D models, or the difference between the 3D model at volume $V_{MAXTD}$, and each intermediate volume $V_{tn}$.

Figure 4B:
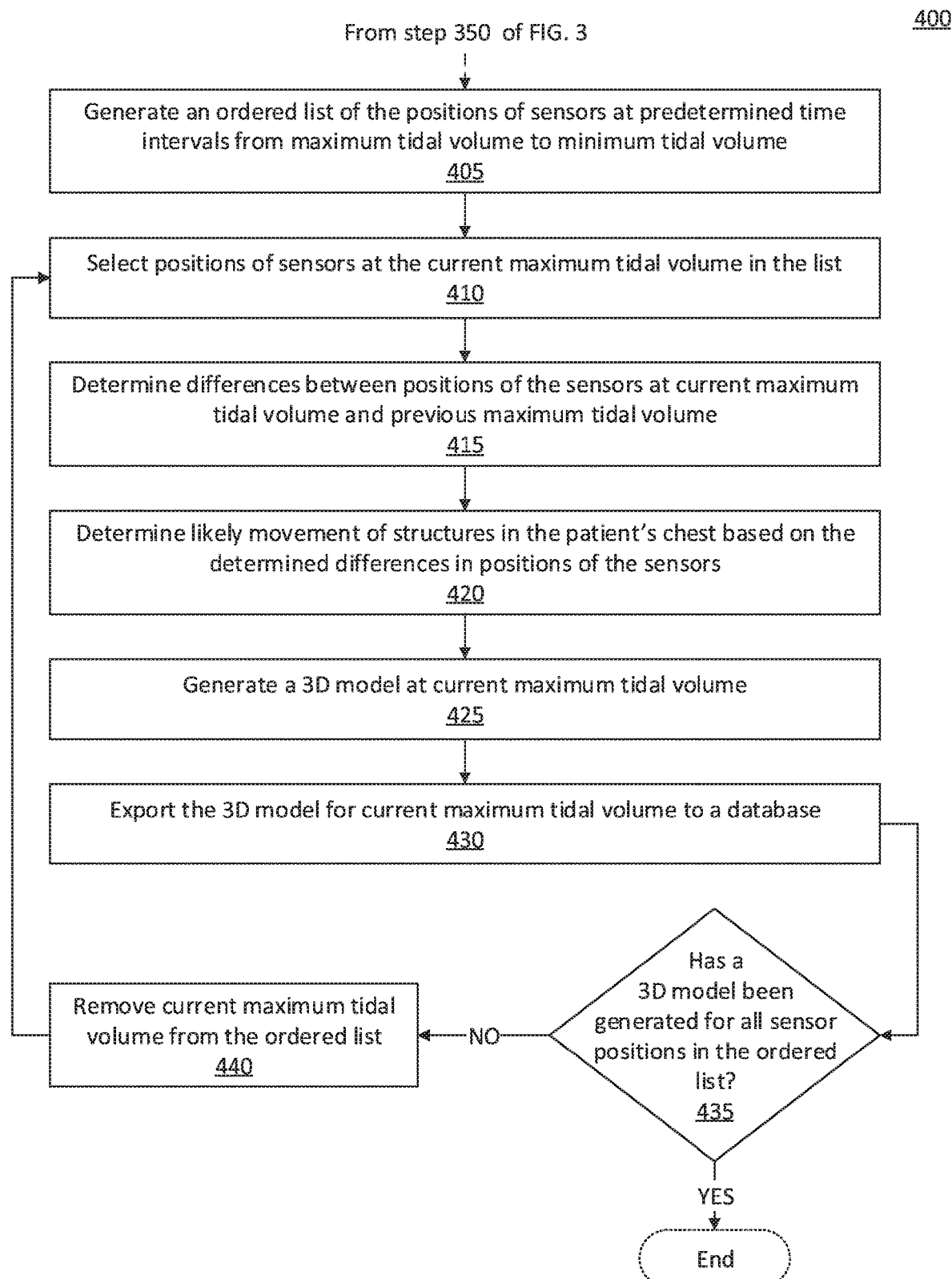
FIG. 4B is a flowchart of example method for pre-procedure 3D model generation based on the positions of a plurality of reference sensors at predetermined time intervals, in accordance with the present disclosure.

Referring now to FIG. 4B, there is shown a flowchart of an illustrative method 400 for determining 3D models, in accordance with embodiments of the present disclosure. Method 400 illustrates steps for generating multiple 3D models based on the volume changes of the thoracic cavity as described in FIG. 4A. Beginning at step 405, the positions of reference sensors 174, determined at predetermined intervals during the patient's respiratory cycle, which were stored in memory 202 at step 320 of FIG. 3, are ordered in a queue or list from the positions of reference sensors 174 at maximum tidal volume to positions of reference sensors 174 at minimum tidal volume (the sensor positions from $V_{t1}$ through $V_{tn}$ of FIG. 4A), excluding positions of reference sensors 174 at $V_{MAXTD}$ and $V_{MINTD}$. It is contemplated that the ordered list of step 405 excludes the positions of reference sensors 174 at maximum tidal volume and the positions of reference sensors 174 at minimum tidal volume which were determined at step 325 of FIG. 3, because 3D models for these positions have already been generated, and because these 3D models are the baselines for generating the simulated 3D models generation steps.

Next, at step 410, the positions of reference sensors 174 at the current maximum tidal volume in the ordered list is determined, and at step 415 the differences between the positions of reference sensors 174 at the current maximum tidal volume in the ordered listed and the positions of reference sensors 174 for the previous maximum tidal volume is determined. For example, during a first iteration though step 415, the differences between the positions of reference sensors 174 at maximum tidal volume ($V_{t1}$ of FIG. 4A) and the positions of reference sensors 174 at the previous maximum tidal volume ($V_{MAXTD}$ of FIG. 4A) are determined.

At step 420, based on the determined differences between the positions of reference sensors 174 at the current maximum tidal volume and positions of reference sensors 174 for the previous maximum tidal volume, the likely movement of structures in the patient's chest, from the positions shown in the 3D model associated with the previously stored positions of reference sensors 174, to positions associated with the current maximum tidal volume, is determined. Next, at step 425, updated simulated 3D model at the current maximum tidal volume is generated and, at step 430, the simulated 3D model at the current maximum tidal volume is stored in database 215. At step 435, a determination is made of whether a 3D model has been generated and stored for all the positions of reference sensors 174 included in the ordered list generated at step 405. If a 3D model has been generated for all positions of reference sensors 174 within the ordered list, method 400 ends. Alternatively, if it is determined at step 435 that a 3D model has not been generated for all positions of reference sensors 174 within the ordered list, method 400 proceeds to step 440 where the current maximum tidal volume in the ordered list is removed. Next, method 400 returns to step 410, where the new current maximum tidal volume in the ordered list is selected. Additionally, if excess movement of the patient or an excursion is detected, an alert may be provided, and the clinician may elect to identify such 'aberrancy' as a cough, yawn, sigh, or other form of expected respiratory event. In the event that such an event is logged as a cough or other expected movement, such movement can be further recorded as part of a labeled event such that a comparison may be made with future events and such that computing device 180 may identify the event.

As illustrated in method 400 and described with reference to FIG. 4A, simulated 3D models may iteratively be generated for each of the positions of reference sensors 174, whether evaluated collectively, individually, or in some other subset or group, as determined at predetermined intervals during the respiratory cycle, which were ordered in a list. Each 3D model is generated based on one or more previously generated 3D models, either in part or in total, and the differences between the positions of reference sensors 174 corresponding to the current 3D model to be generated and the positions of reference sensors 174 corresponding to the previous 3D model, which was previously generated. Thus, incrementally, simulated 3D models may be generated during each of the predetermined intervals. Additionally, since the 3D models are generated dynamically based on determined incremental differences between at least two known positions, a 3D model may be generated for any potential time interval. Further, a dynamically moving 3D model simulation may be generated based on the above-described 3D models to create a "moving" image of the 3D models that changes with the patient's respiratory cycle.

Figure 5:
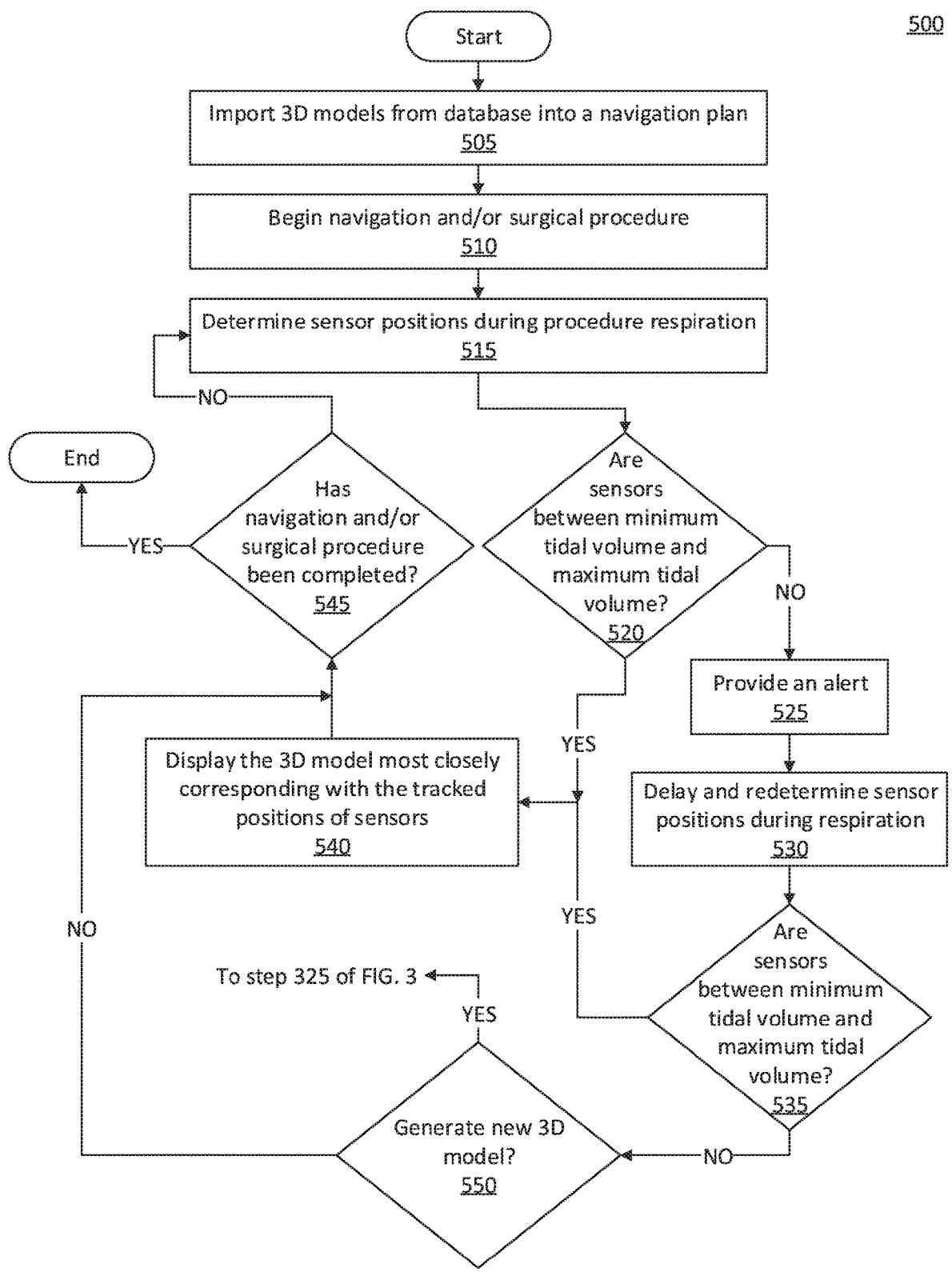
FIG. 5 is a flowchart of an example method for an intra-procedure 3D model generation based on the positions of a plurality of reference sensors, in accordance with the present disclosure.

Referring now to FIG. 5, there is shown a flowchart of an illustrative method 500 for intra-procedure 3D model selection and generation, in accordance with embodiments of the present disclosure. Starting at step 505, a navigation plan, including the 3D models of the interior of the patient which were generated from methods 300 and 400, is loaded into computing device 180.

Next, at step 510, the clinician begins navigation and/or a surgical procedure while the patient breathes normally. Positions of reference sensors 174, attached to the patient prior to the start of the procedure, are determined at step 515 and tracked throughout the procedure.

Additionally, although not shown in method 500, prior to navigation, a clinician may perform automatic registration. An example of registration includes the clinician advancing bronchoscope 150, locatable guide 192, and EWC 196 into each region of the patient's airways until sufficient data points representing the position of EM sensor 194 of locatable guide 192 within the patient's airways have been obtained to register the 3D model with the patient's airways. Details of such registration techniques are set forth in U.S. Patent Publication No. 2016/0000356 entitled "REAL-TIME AUTOMATIC REGISTRATION FEEDBACK," filed on Jul. 2, 2015, by Brown et al., the entire contents of which are incorporated herein by reference.

Next, at step 520, processor 204 determines whether the determined positions of reference sensors 174 are between the maximum tidal volume and minimum tidal volume determined at step 325 of FIG. 3. For example, processor 204 may determine whether differences between the positions of reference sensors 174 determined at step 515 and the positions of reference sensors 174 at maximum tidal volume (determined at step 325) are less than the differences between the positions of reference sensors 174 at maximum tidal volume and the positions of reference sensors 174 at full-breath hold (determined at step S335) to determine that the positions of reference sensors 174 determined at step 515 are not between the maximum tidal volume and the minimum tidal volume. Likewise, processor 204 may determine whether differences between the positions of reference sensors 174 determined at step 515 and the positions of reference sensors 174 at minimum tidal volume (determined at step 325) are greater than the differences between the positions of reference sensors 174 at minimum tidal volume and the positions of reference sensors 174 at full-breath hold (determined at step S335) to determine that the positions of reference sensors 174 determined at step 515 are not between the maximum tidal volume and the minimum tidal volume. If, at step 520, it is determined that the determined positions of reference sensors 174 are between the maximum tidal volume and minimum tidal volume, method 500 proceeds to step 540 where the 3D model most closely corresponding to the positions of reference sensors 174 is displayed. Additionally or alternatively, one or more individual reference sensors 174 or groups of reference sensors 174 may be selected, and only data regarding the position of such reference sensors 174 may be evaluated to determine which 3D model to be displayed. For example, the individual or groups of reference sensors 174 may be selected based on a displayed portion of the 3D model and/or a region of interest. Next, method 500 proceeds to step 545 where it is determined whether navigation and/or the surgical procedure has been completed. If navigation and/or the surgical procedure has been completed, method 500 ends. If it is determined at step 545 that navigation and/or the surgical procedure has not been completed, method 500 returns to step 515 where new positions of reference sensors 174 is determined. Thus, steps 515-520-540-545-515 of method 500 allow a clinician to visualize multiple 3D models of the patient's chest where each 3D model corresponds to the positions of reference sensors 174 during particular phases or points of the patient's respiratory cycle. The result is a video-like display of the 3D models as they change during respiration of the patient from maximum to minimum tidal volume breathing.

If, at step 520, it is determined that the detected positions of reference sensors 174, whether collectively, individually, or in various subsets or groups, are not between the maximum tidal volume and minimum tidal volume, method 500 proceeds to step 525 where an alert is provided to the clinician. The alert may be audible, tactile and/or visual, and provide the clinician with a notification that the movement of reference sensors 174 is outside of the maximum tidal volume and minimum tidal volume and therefore the 3D models which may be displayed may be less accurate. In some embodiments, prior to providing the alert to the clinician, processor 204 may determine whether the reference sensors 174 for which positions that are not between the maximum and minimum tidal volume are detected are within a predetermined distance of the region of interest. Processor 204 may then exclude reference sensors 174 that are more than the predetermined distance of the region of interest from causing an alert to be provided. For example, processor 204 may provide the alert only if an individual or group of reference sensors 174 within a predetermined distance of the region of interest have detected positions that are not between the maximum and minimum tidal volume. Processor 204 may also apply different weights to different reference sensors 174. For example, reference sensors 174 that are closer to the region of interest may be weighted heavier than reference sensors 174 that are further away from the region of interest. Thus, when reference sensors 174 have detected positions that correspond to different phases or points in the patient's respiratory cycle, processor 204 may select an updated 3D model based on detected positions of reference sensors 174 closer to the region of interest rather than detected positions of reference sensors 174 further away from the region of interest. Similarly, when reference sensors 174 further away from the region of interest have detected positions that are not between the maximum and minimum tidal volume, processor 204 may ignore and/or deactivate such reference sensors 174.

Next, at step 530, a delay may be utilized to determine whether the positions of reference sensors 174 outside of the maximum tidal volume and minimum tidal volume were due to sporadic sensor movement, such as a cough or non-respiratory movement of the patient. The delay may be based on a single full respiratory cycle or multiple respiratory cycles. Following the delay, the positions of reference sensors 174 are again determined and, at step 535, it is determined whether the positions of reference sensors 174 are between of the maximum tidal volume and minimum tidal volume. If, at step 535, it is determined that the positions of reference sensors 174 are between the maximum tidal volume and minimum tidal volume, method 500 proceeds to step 540 where the 3D model most closely corresponding to the positions of reference sensors 174 is displayed.

If, at step 535, it is determined that the positions of reference sensors 174 are not between the maximum tidal volume and minimum tidal volume, method 500 proceeds to step 550 where it is determined whether anew 3D model should be generated. An alert may be provided to the clinician indicating that intra-procedure respiration exceeds the 3D models which were imported at step 505. The clinician may then provide input to computing device 180 indicating whether new 3D models at maximum tidal volume and/or minimum tidal volume should be generated. If, at step 550, computing device 180 receives input to update the 3D models, method 500 returns to step 325 of FIG. 3, where a new maximum tidal volume and/or minimum tidal volume are determined and new 3D models are generated and stored. If, at step 550, the clinician opts not to generate new 3D models, and thus computing device 180 does not receive input to update the 3D models, method 500 proceeds to step 545.

Figure 6:
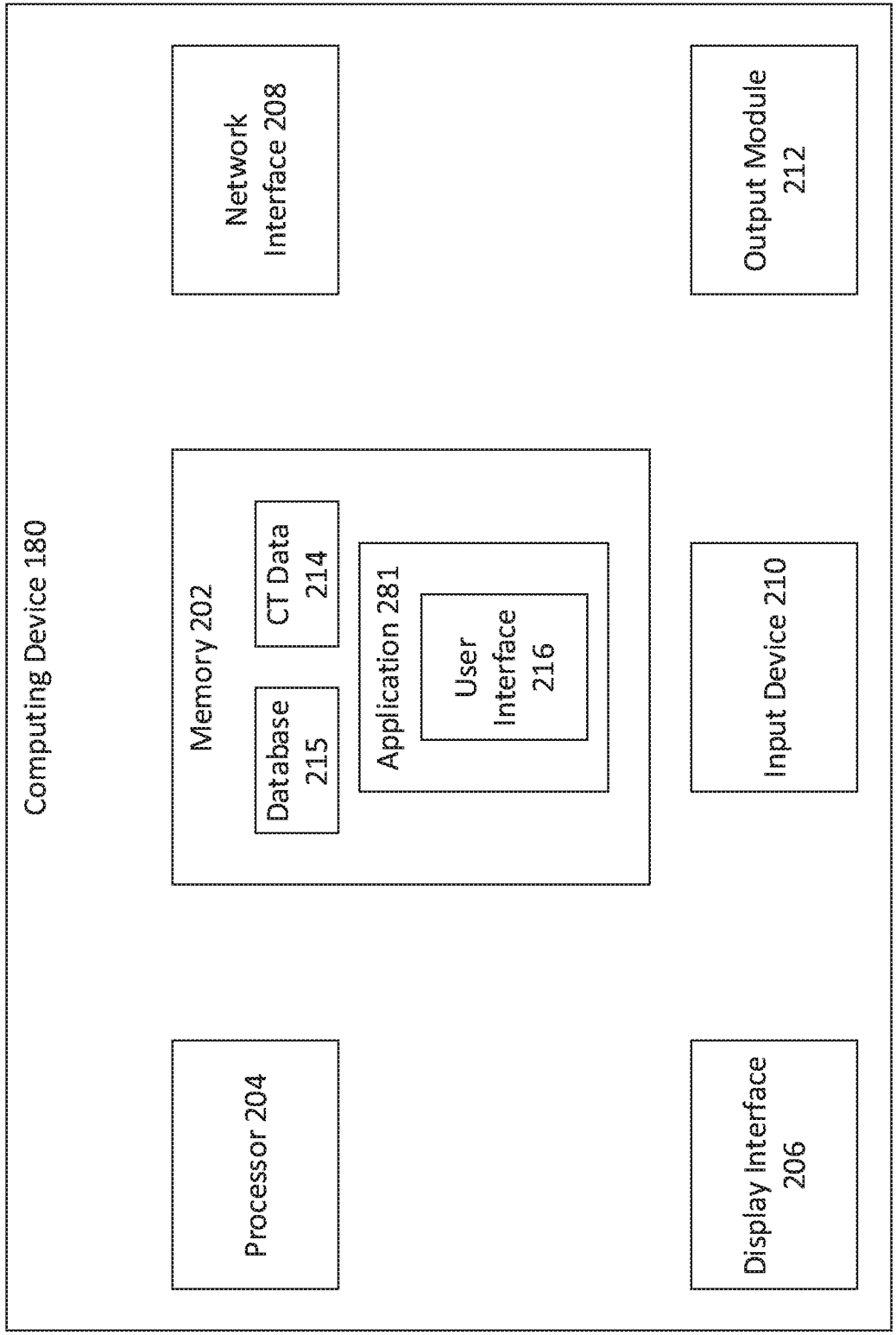
FIG. 6 is a schematic diagram of a computing device configured for use with the system of FIG. 1, in accordance with the present disclosure.

Turning now to FIG. 6, a diagram of computing device 180 is illustrated. Computing device 180 may include a memory 202, which further includes CT image data 214, a database 215, and an application 281 including a user interface module 216. Computing device 180 further includes at least one processor 204, a display interface 206, a network interface 208, an input device 210, and/or an output module 212. In some embodiments, database 215 is stored in a different computing device and connected to computing device 180 via network interface 208.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to employ the present disclosure in virtually any appropriately detailed structure. While the preceding embodiments were described in terms of bronchoscopy of a patient's airways, those skilled in the art will realize that the same or similar devices, systems, and methods may be used in other lumen networks, such as, for example, the vascular, lymphatic, and/or gastrointestinal networks as well.

What is claimed is:

1. A system for visualizing movement of structures within a patient's chest, the system comprising:
    an electromagnetic (EM) tracking system including:
        an EM field generator configured to generate an EM field;
        a plurality of EM sensors attached to a patient and movable within the EM field; and
        a tracking module configured to detect positions of the plurality of EM sensors within the EM field;
    a display device; and
    a computing device including:
        a processor; and
        a memory storing instructions which, when executed by the processor, cause the computing device to:
            receive a plurality of images of the patient's chest;
            generate a first (three-dimensional) 3D model of an interior of the patient's chest based on the plurality of images of the patient's chest;
            determine positions of the plurality of EM sensors at full-breath hold;
            determine positions of the plurality of EM sensors at maximum tidal volume;
            determine differences between the positions of the plurality of EM sensors at maximum tidal volume and the positions of the plurality of EM sensors at full-breath hold;
            generate a second 3D model at maximum tidal volume based on the differences between the positions of the plurality of EM sensors at maximum tidal volume and the positions of the plurality of EM sensors at full-breath hold; and
            cause the display device to display the second 3D model.

2. The system according to claim 1, wherein the instructions, when executed by the processor, further cause the computing device to:
    determine positions of the plurality of EM sensors at minimum tidal volume;
    determine differences between the positions of the plurality of EM sensors at minimum tidal volume and the positions of the plurality of EM sensors at maximum tidal volume; and
    generate a third 3D model at minimum tidal volume based on the differences between the positions of the plurality of EM sensors at minimum tidal volume and the positions of the plurality of EM sensors at maximum tidal volume.

3. The system according to claim 2, wherein the instructions, when executed by the processor, further cause the computing device to:
generate an ordered list of sets of positions of the plurality of EM sensors at predetermined intervals, wherein the ordered list excludes the positions of EM sensors at maximum tidal volume and minimum tidal volume;
select a first set of positions of the plurality of EM sensors from the ordered list;
determine differences between the selected first set of positions of the plurality of EM sensors and positions of the plurality of EM sensors at maximum tidal volume; and
generate a fourth 3D model based on the differences between the selected first set of positions of the plurality of EM sensors and the positions of the plurality of EM sensors at maximum tidal volume.

4. The system according to claim 3, wherein the instructions, when executed by the processor, further cause the computing device to:
select a subset of EM sensors from the plurality of EM sensors, the subset of EM sensors corresponding to a region of the patient's chest;
determine current positions of the subset of EM sensors;
determine differences between the current positions of the subset of EM sensors and the positions of the subset of EM sensors during maximum tidal volume, minimum tidal volume, and the selected first position of the plurality of EM sensors; and
cause the display device to display one of the second, third, or fourth 3D models based on the determined differences between the current positions of the subset of EM sensors and the positions of the subset of EM sensors during maximum tidal volume, minimum tidal volume, and the selected first positions of the plurality of EM sensors.

5. The system according to claim 2, wherein the instructions, when executed by the processor, further cause the computing device to:
determine current positions of the plurality of EM sensors;
determine differences between the current positions of the plurality of EM sensors and the positions of the plurality of EM sensors at maximum tidal volume or the positions of the plurality of EM sensors at minimum tidal volume;
determine that differences between the current positions of the plurality of EM sensors and the positions of the plurality of EM sensors at maximum tidal volume is less than the differences between the positions of the plurality of EM sensors at full-breath hold and the positions of the plurality of EM sensors at maximum tidal volume, or that differences between the current positions of the plurality of EM sensors and the positions of the plurality of EM sensors at minimum tidal volume is greater than the differences between the positions of the plurality of EM sensors at full-breath hold and the positions of the plurality of EM sensors at minimum tidal volume; and
generate a fifth 3D model based on the differences between the current positions of the plurality of EM sensors and the positions of the plurality of EM sensors at maximum tidal volume or the positions of the plurality of EM sensors at minimum tidal volume.

6. The system according to claim 1, wherein the instructions, when executed by the processor, further cause the computing device to:
determine intra-procedure positions of the plurality of EM sensors at a predetermined interval during a surgical procedure; and
determine whether the intra-procedure positions of the plurality of EM sensors exceed the positions of the plurality of EM sensors at minimum tidal volume or the positions of EM sensors at maximum tidal volume.

7. The system according to claim 6, wherein the instructions, when executed by the processor, further cause the computing device to:
select a 3D model corresponding to the intra-procedure positions of the plurality of EM sensors, when it is determined that the intra-procedure positions of the plurality of EM sensors do not exceed the positions of the plurality of EM sensors at minimum tidal volume and the positions of EM sensors at maximum tidal volume.

8. The system according to claim 6, wherein the instructions, when executed by the processor, further cause the computing device to:
generate a new 3D model at maximum tidal volume or a new 3D model at minimum tidal volume, when it is determined that the intra-procedure positions of the plurality of EM sensors exceed the positions of the plurality of EM sensors at minimum tidal volume or the positions of the plurality of EM sensors at maximum tidal volume.

9. The system according to claim 6, wherein the instructions, when executed by the processor, further cause the computing device to:
provide an alert when it is determined that the intra-procedure positions of the plurality of EM sensors exceed the positions of the plurality of EM sensors at minimum tidal volume or the positions of the plurality of EM sensors at maximum tidal volume.

10. The system according to claim 1, wherein the plurality of images of the patient's chest are obtained during a full-breath hold CT scan.

11. A method for visualizing movement of structures within a patient's chest, the method comprising:
receiving a plurality of images of a patient's chest;
tracking positions of a plurality of electromagnetic (EM) sensors attached to the patient and movable within an EM field generated by an EM field generator;
generating a first 3D model of an interior of the patient's chest based on the plurality of images of the patient's chest;
determining positions of a plurality of EM sensors at full-breath hold;
determining positions of the plurality of EM sensors at maximum tidal volume;
determining differences between the positions of the plurality of EM sensors at maximum tidal volume and the positions of the plurality of EM sensors at full-breath hold;
generating a second 3D model at maximum tidal volume based on the differences between the positions of the plurality of EM sensors at maximum tidal volume and the positions of the plurality of EM sensors at full-breath hold; and
displaying the second 3D model.

12. The method according to claim 11 further comprising:
determining positions of the plurality of EM sensors at minimum tidal volume;

determining differences between the positions of the plurality of EM sensors at minimum tidal volume and the positions of the plurality of EM sensors at maximum tidal volume; and generating a third 3D model at minimum tidal volume based on the differences between the positions of the plurality of EM sensors at minimum tidal volume and the positions of the plurality of EM sensors at maximum tidal volume.

13. The method according to claim 12, further comprising:

generating an ordered list of sets of positions of the plurality of EM sensors at predetermined intervals, wherein the ordered list excludes the positions of EM sensors at maximum tidal volume and minimum tidal volume;

selecting a first set of positions of the plurality of EM sensors from the ordered list;

determining differences between the selected first set of positions of the plurality of EM sensors and positions of the plurality of EM sensors at maximum tidal volume; and generating a fourth 3D model based on the differences between the selected first set of positions of the plurality of EM sensors and the positions of the plurality of sensors at maximum tidal volume.

14. The method according to claim 13, further comprising:

selecting a subset of EM sensors from the plurality of EM sensors, the subset of EM sensors corresponding to a region of the patient's chest;

determining current positions of the subset of EM sensors;

determining differences between the current positions of the subset of EM sensors and the positions of the subset of EM sensors during maximum tidal volume, minimum tidal volume, and the selected first position of the plurality of EM sensors; and displaying one of the second, third, or fourth 3D models based on the determined differences between the current positions of the subset of EM sensors and the positions of the subset of EM sensors during maximum tidal volume, minimum tidal volume, and the selected first position of the plurality of EM sensors.

15. The method according to claim 14, further comprising:

determining current positions of the plurality of EM sensors;

determining differences between the current positions of the plurality of EM sensors and the positions of the plurality of EM sensors at maximum tidal volume or the positions of the plurality of EM sensors at minimum tidal volume;

determining that differences between the current positions of the plurality of EM sensors and the positions of the plurality of EM sensors at maximum tidal volume is less than the differences between the positions of the plurality of EM sensors at full-breath hold and the positions of the plurality of EM sensors at maximum tidal volume, or that differences between the current positions of the plurality of EM sensors and the positions of the plurality of EM sensors at minimum tidal volume is greater than the differences between the positions of the plurality of EM sensors at full-breath hold and the positions of the plurality of EM sensors at minimum tidal volume; and generating a fifth 3D model based on the differences between the current positions of the plurality of EM sensors and the positions of the plurality of EM sensors at maximum tidal volume or the positions of the plurality of EM sensors at minimum tidal volume.

16. The method according to claim 11, further comprising:

determining intra-procedure positions of the plurality of EM sensors at a predetermined interval during a surgical procedure; and determining whether the intra-procedure positions of the plurality of EM sensors exceed the positions of the plurality of EM sensors at minimum tidal volume or the positions of EM sensors at maximum tidal volume.

17. The method according to claim 16, further comprising generating a new 3D model at maximum tidal volume or a new 3D model at minimum tidal volume, when it is determined that the intra-procedure positions of the plurality of EM sensors exceed the positions of the plurality of EM sensors at minimum tidal volume or the positions of the plurality of EM sensors at maximum tidal volume.

18. The method according to claim 16, further comprising:

providing an alert, when it is determined that the intra-procedure positions of the plurality of EM sensors exceed the positions of the plurality of EM sensors at minimum tidal volume or the positions of the plurality of EM sensors at maximum tidal volume.

19. The method according to claim 11, further comprising:

selecting a 3D model corresponding to the intra-procedure positions of the plurality of EM sensors, when it is determined that the intra-procedure positions of the plurality of EM sensors do not exceed the positions of the plurality of EM sensors at minimum tidal volume and the positions of EM sensors at maximum tidal volume.

20. The method according to claim 11, wherein the plurality of images of the patient's chest are obtained during a full-breath hold CT scan.

* * * * *